United States Patent [19]
O'Phelan

[11] Patent Number: 5,383,914
[45] Date of Patent: Jan. 24, 1995

[54] DIAGNOSTIC CONNECTOR PORT FOR A PULSE GENERATOR

[75] Inventor: Michael O'Phelan, Roseville, Minn.

[73] Assignee: Cardiac Pacemakers, Inc., St. Paul, Minn.

[21] Appl. No.: 177,659

[22] Filed: Jan. 5, 1994

Related U.S. Application Data

[63] Continuation of Ser. No. 882,524, May 13, 1992, abandoned.

[51] Int. Cl.⁶ ............................................. A61N 1/00
[52] U.S. Cl. .................................................. 607/38
[58] Field of Search .............................. 607/37, 36, 38

[56] References Cited

U.S. PATENT DOCUMENTS 4,479,489 10/1984 Tucci .
4,774,951 10/1988 Osypka .
4,898,173 2/1990 Daglow et al. .................. 128/419 P

FOREIGN PATENT DOCUMENTS 0205737 2/1986 European Pat. Off. .
2178152 11/1973 France .
3233031A1 6/1983 Germany .

Primary Examiner—Lee S. Cohen
Assistant Examiner—Marianne H. Parker
Attorney, Agent, or Firm—Keck, Mahin & Cate

[57] ABSTRACT

A diagnostic connector port is premolded into a header of a pulse generator device. A diagnostic connector port is attached to each of the electrical contacts in the header and does not measurably affect the system resistance. The diagnostic connector port is sealed against body fluids or other external, conductive fluids. Excellent electrical contact is achieved via a special connector pin/socket design. The diagnostic connector port is keyed for one way only insertion of the external diagnostic equipment into the diagnostic connector port.

22 Claims, 9 Drawing Sheets

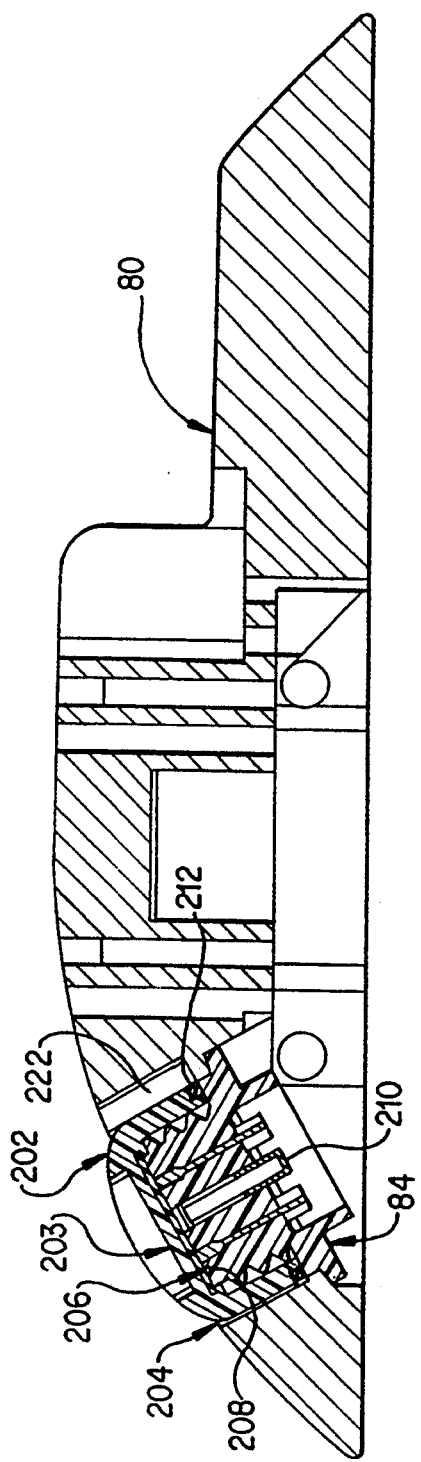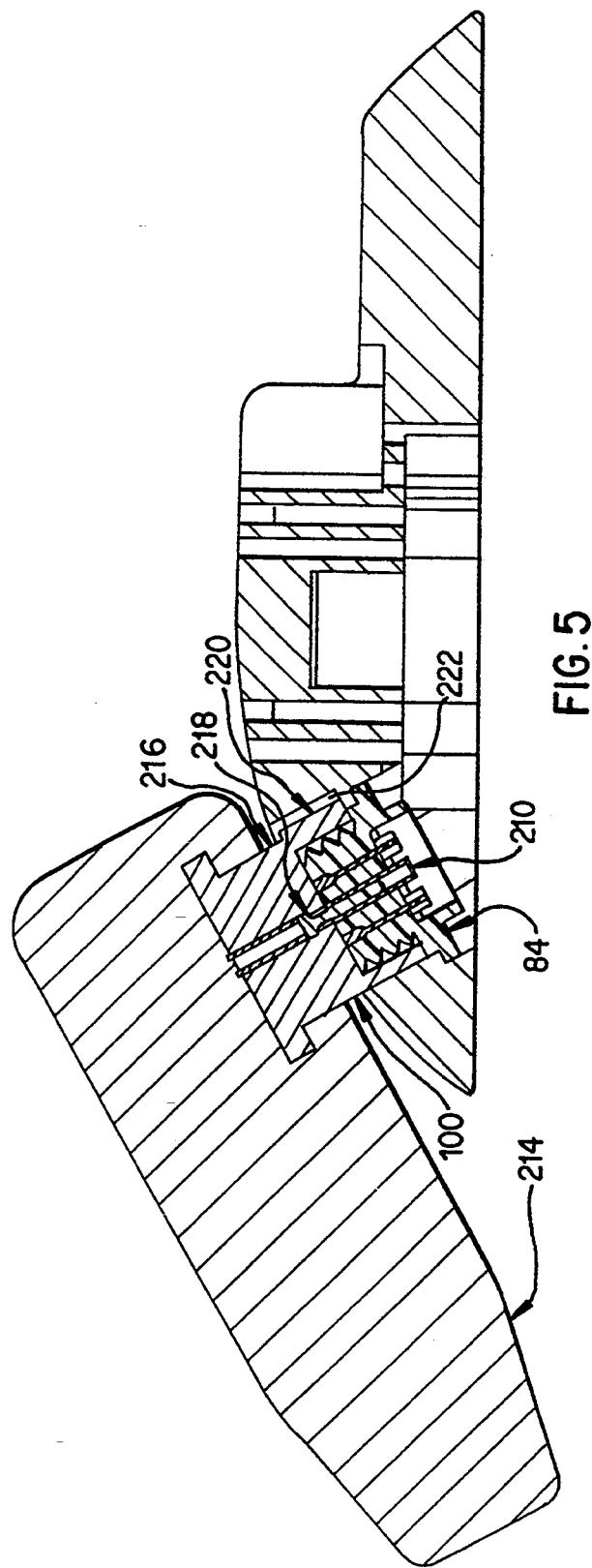
FIG. 4
FIG. 5

| | |
|---|---|
| DEFIB NEGATIVE PORT PIN | P6 — C6 DEFIB NEGATIVE CONNECTOR BLOCK |
| ATRIAL TIP PORT PIN | P5 — C5 ATRIAL TIP CONNECTOR BLOCK |
| ATRIAL RING PORT PIN | P4 — C4 ATRIAL RING CONNECTOR BLOCK |
| DEFIB POSITIVE PORT PIN | P3 — C3 DEFIB POSITIVE CONNECTOR BLOCK |
| VENTRICAL RING PORT PIN | P2 — C2 VENTRICAL RING CONNECTOR BLOCK |
| VENTRICAL TIP PORT PIN | P1 — C1 VENTRICAL TIP CONNECTOR BLOCK |

DIAGNOSTIC CONNECTOR PORT FOR A PULSE GENERATOR

This application is a continuation of U.S. patent application Ser. No. 07/882,524, filed May 13, 1992 now abandoned.

FIELD OF THE INVENTION

The present invention includes a diagnostic connector port implanted with a pulse generator device serving as an implant aid to monitor device leads while the leads are plugged into a header of the pulse generator device It is possible to sense, pace, defibrillate, and monitor the lead/device electrical signals while the patient leads are in place in the device header.

BACKGROUND OF THE INVENTION

Many of the early concepts for monitoring the lead/device electrical signals of a pulse generator device failed due to complexity, potential sealing problems or due to size constraints. Currently, monitoring of lead/device electrical signals is achieved by one of two methods.

The first method requires hex shaped drivers to be inserted through seal plugs into a hexagon shaped opening of a set screw of a pulse generator device. The hexagon shaped driver is then electrically connected to various external equipment via an alligator clip/wire attached to a metal shaft of the hexagon shaped driver.

The disadvantages of such an approach are:

1. Poor electrical contact made between hex driver and set screw head.
2. Plurality of alligator clips causes both confusion on diagnostic end of cables and possibility of shorts between the tightly spaced alligator clips on limited space of the shaft of the hexagon shaped driver.
3. Method is extremely cumbersome.
4. Damage to seal plugs is dependent on the number of insertions. Each extra insertion to test the device reduces the reliability of the seal.
5. If all the ports of the device need to be monitored at the same time, the physician must have multiple set screws, clips, and cable arrangements on hand.
6. The time required to make electrical contact to the device is lengthy thereby increasing the time the wound is exposed which increases patient risk and the possibility of infection.
7. High voltage signals sent through poor contacts may be shunted, resulting in reduced defibrillation energy being delivered to the heart.
8. Movement of the cable causes noise spikes in electrical contacts.

In the second method, electrical contact to the pulse generator device is made in essentially the same way and the same problems persist. By this method, opposed clamps are inserted into opposed sealed plugs. The opposed clamps are tensioned towards each other by rubber bands which force contact of the clamps into the diagnostic blocks after passing through seals. The inward force on the opposed clamps causes a loosening of the clamps. Slight movements of the cable show up as noise spikes on the supporting diagnostic equipment. Although this is an improvement over the first method approach, the same problems remain.

SUMMARY OF THE INVENTION

The present invention overcomes all of the problems associated with the prior approaches.

The present invention incorporates a custom designed diagnostic connector port into a premolded top of any implantable pulse generator product. A diagnostic connector port is attached in parallel with each of the electrical contacts in the header. It is a permanent connection to these contacts and is therefore implanted with the device and is sealed against body fluids or other external, conductive fluids.

Excellent electrical contact is achieved via a special connector pin/socket design. It is intended that the pin/socket connection will be strong enough to mechanically hold an output cable in place as well. However, the mechanical holding of the output cable could be achieved in a variety of ways.

The opposite end of the output cable (diagnostic side) will be a standard connector, but could also be any number of standard/non-standard connection schemes to achieve a suitable interface to the external diagnostic equipment. The diagnostic connector port will be keyed for alignment as to which pin is which and to provide one way only insertion to the external diagnostic equipment.

The new approach of this invention is not at all cumbersome. It is a simple, keyed, snap-in type of connection and takes fractions of a second to install. It will not damage the seal plugs since it does not rely on their presence to achieve electrical contact. In fact, it is possible that there will not be access through a seal plug due to the variety and integrity of toolless connection schemes becoming available for implantable pulse generators.

The plurality of parts problem is overcome by virtue of a single cable/contact to achieve connections to all electrical contacts at the same time.

High voltage signals will be allowed through a single diagnostic connector port. This will be achieved by choosing appropriate material dielectric constants as well as proper pin spacing. Due to high pin contact force, mechanical movement of the cable is not expected to cause noise spikes. The connector assembly has a 0.050" max pin spacing and the pins may be made of platinum, titanium, niobium or possibly stainless steel. The pin to pin resistance is at least 50,000 ohms and the voltage breakdown potential is at least 1000 volts.

The entire diagnostic connector port is manufactured from biomedically compatible materials. The port assembly is molded into a polyurethane part so the material surrounding the pins would be both compatible with the molding process and be bio-compatible. A polyurethane material would comply with these requirements. The entire assembly is sealed from an external (body fluid) environment which is at 37° C.

The single diagnostic connector port is connected to diagnostic equipment with a single cable assembly. The interconnection is simple to use yet reliable in design.

It is an object of the invention to provide a pulse generator device with a diagnostic port connector which is attached to each of the electrical contacts in a header of the pulse generator device.

It is another object of the invention to provide a pulse generator device with a diagnostic port connector which is attached to each of the electrical contacts in a header of the pulse generator device for monitoring of lead/device electrical signals by an output cable connected to the diagnostic port connector and external diagnostic equipment.

It is still yet another object of the invention to provide a pulse generator device with a diagnostic port connector which is attached to each of the electrical contacts in a header of the pulse generator device for monitoring of lead/device electrical signals by an output cable connected to the diagnostic port connector and external diagnostic equipment with a sealing plug covering the diagnostic connector port against contact with body fluids.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 4 is a sectional view of the details of the diagnostic port with its sealing plug and cap.

FIG. 5 is a cable/port sectional view with the cable plugged into the diagnostic port.

DETAILED DESCRIPTION OF THE PREFERRED EMBODIMENTS

Figure 1:
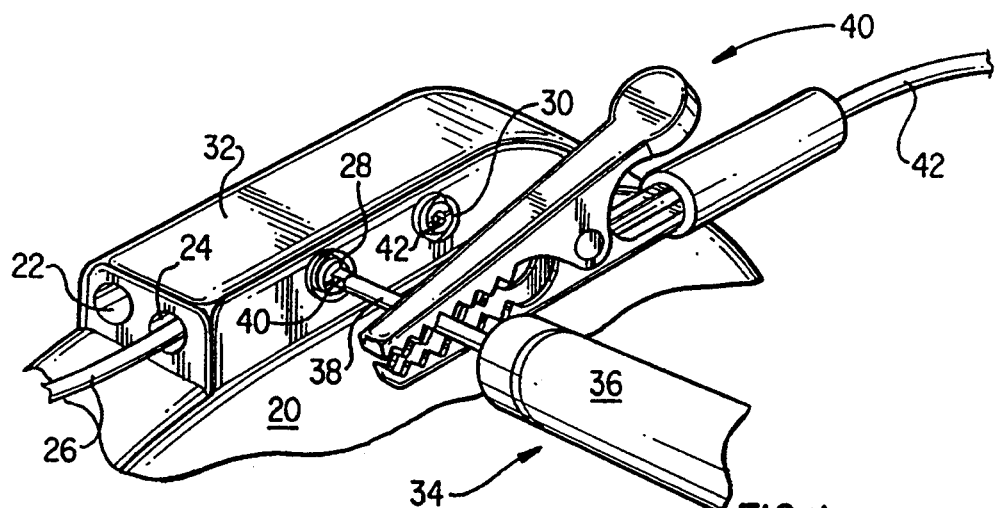
FIGS. 1 and 2 are illustrative examples of prior known techniques for the monitoring of diagnostic information produced by a pulse generator device.

In describing a preferred embodiment of the invention illustrated in the drawings, specific terminology will be resorted to for the sake in clarity. However, the invention is not intended to be limited to the specific terms so selected, and it is to be understood that each specific term includes all technical equivalents which operate in a similar manner to accomplish a similar purpose.

Figure 2:
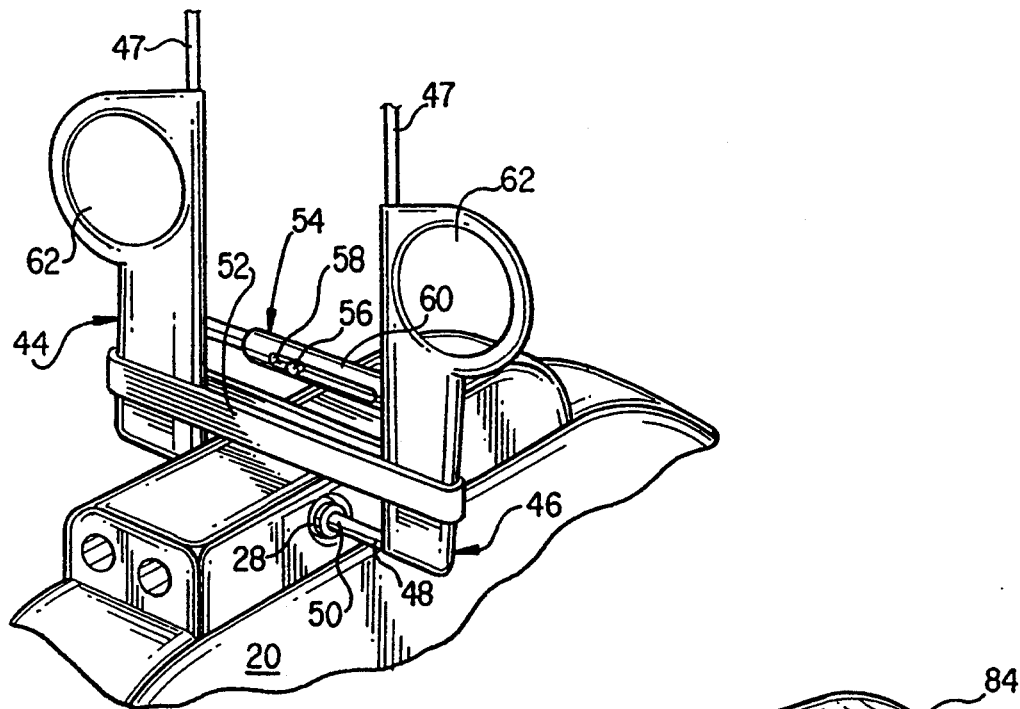

With reference to the drawings, in general, and to FIGS. 1 and 2 in particular, prior known systems for receiving diagnostic signals generated by a pulse generator are shown.

In FIG. 1, a pulse generator device 20 includes ports 22 and 24 to which leads are connected which extend to electrodes implanted in the heart. Lead 26 is shown extending into port 24 as an example. Set screws 28 and 30 are threaded into connector blocks in the header 32 of the pulse generator device 20. Each of the set screws 28 and 30 are covered by a flexible seal material (not shown for the purposes of clarity) to isolate the set screws 28 and 30 from interaction with surrounding body fluids.

To obtain signals from the set screws 28, 30, a tool 34 having handle 36 and metal shaft 38 terminating in a hexagonally-shaped head 40, is inserted into a hexagonally-shaped opening 42 of the set screws 28 or 30. The connection between the metal shaft 38 and the hexagonally-shaped opening 42, after passage through the seal material covering the set screws 28 or 30, allows transmission of the signals from the pulse generator device 20 to the shaft 38.

Attached to the shaft 38 is an alligator clip 40 having lead 42 connected to a device which will interpret the signals being transferred through the set screws 28 or 30 to the shaft 38, and by the connection of the alligator clip 40 to the shaft transmission of signals over electrically connected lead 42. As discussed above, there are many disadvantages to this system.

Another known system has made use of the same type of arrangement as shown for set screw 28 of a pulse generator device 20 as shown in FIG. 2 by connection of opposed clamps 44 and 46, having shaft 48 with spherical-shaped terminal portion 50 for insertion into a set screw 28. A connection lead 47 extends through clamps 44 and 46 to shafts 48. Leads 47 transmit signals received by shafts 48.

The clamps 44 and 46 are biased toward each other by an elastic member 52 and are stabilized with respect to each other by an interengaging slide assembly 54, having a projecting pin 56 of clamp 44 sliding within a groove 58 of a hollow member 60 of clamp 46. Finger openings 62 are located at the ends of each of the clamps 44 and 46 for biased movement of the two clamps 44 and 46 toward each other. This system, although an improvement over the system of FIG. 1, includes the same disadvantages.

Figure 3:
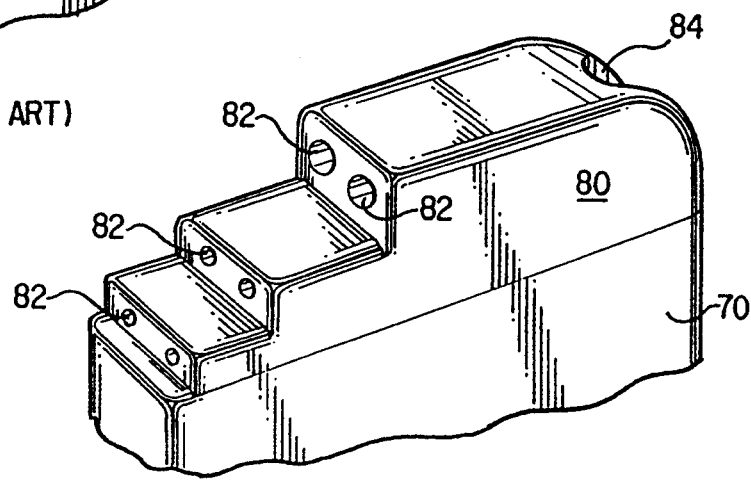
FIG. 3 is a perspective view of a pulse generator device having a diagnostic connector port.

With reference to FIGS. 3 through 14 and 21, a preferred embodiment of a diagnostic port connector embodying the teachings of the subject invention is shown. In FIG. 3, a pulse generator device 70, having a molded header 80, includes six ports 82 for leads connected to electrodes implanted in the heart. In the embodiment shown in FIG. 3, a diagnostic port connector 84 is shown located at the rear of the header 80. Alternately, as shown in other Figures the diagnostic port connector 84 may be located at one of several different locations spaced about the header of the pulse generator device 70. In all embodiments, it is possible to use the diagnostic port to access the completed device in its sterile packaging for pre-implant studies with the device.

Figure 7:
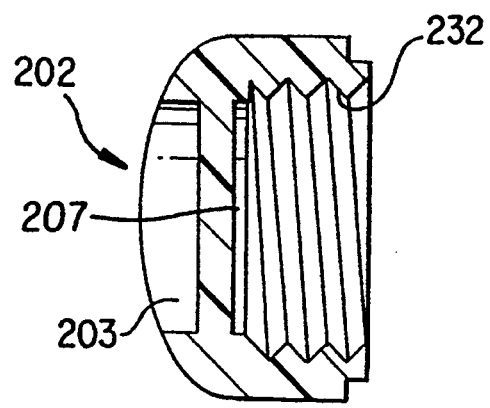
FIG. 7 is a sectional view of the plug for the diagnostic port.

In FIG. 4, a diagnostic port cap 202 is screwed onto the body of the diagnostic port 84 to force body fluid out of the cavity 204. A facial seal or sealing plug 206 interfaces with a flat surface 208 of the diagnostic port 84 and an indented region 207 (as shown in FIG. 7) of the port cap 202 to "squeeze" out any fluids at this interface. A plurality of female-type contact receptacles 210 are slightly recessed from the surface 208 to prevent dendritic growth. When the internally threaded diagnostic port cap 202 is tightened downwardly by screwdriver slot 203 around the externally threaded diagnostic port, the cap prevents current from flowing from receptacle 210 to receptacle 210. A O-ring seal area 212 is an optional additional seal to seal plug 206 to decrease a chance of failure of the sealing system.

In FIG. 5, a detailed view of a cable/port interconnection is shown. A cable block 214 is plugged into the diagnostic port 84. A stainless steel sleeve 216 of a connector plug 100 is imbedded in one end of the cable block 214 serves to both protect the male-type interface pins 218 and to align the cable block 214 in the diagnostic port 84. The pins 218 are slightly recessed within the sleeve 216 to allow key 220 of sleeve 216 to engage in keyway 222 for proper alignment prior to pin 218/contact receptacle 210 interconnection. The cable 214 can be locked in place and/or sealed, if desired.

Figure 6:
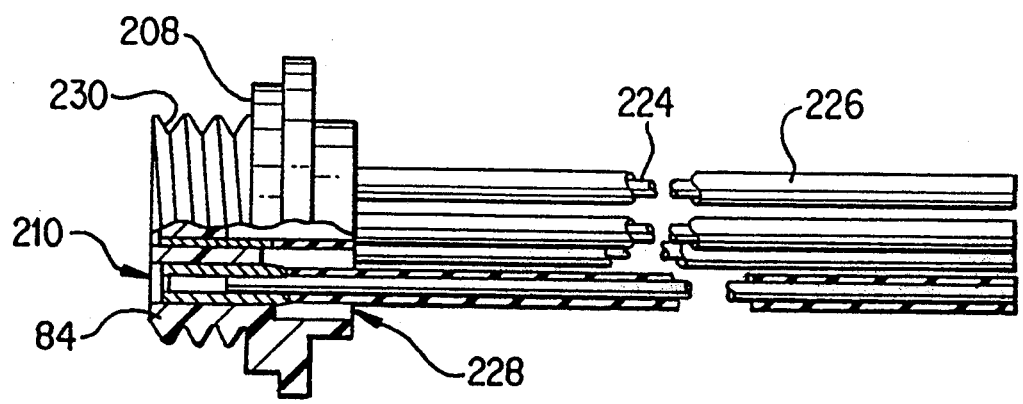
FIG. 6 is a partial sectional view of the diagnostic port and its connecting lead lines.

FIGS. 6 and 7 show details of the diagnostic port 84 and its connector cap 202. The diagnostic port 84 may be made of a body material such as polyurethane which is commercially available from Dow Chemical under the trademark Pellethane 2363. The wires 224 connected to the female contact receptacles 210 are 0.018 inch platinum wire. The female contact receptacle 210 is made of titanium TI-6AL-4V. The wires 224 are insulated by tubing material 226, such as polyimide tubing. A gap 228 at the rear of the diagnostic port is back-filled with an epoxy-type material.

External threads 230 of the diagnostic port are shown for interengagement with internal threads 232 of port connector cap 202. Port connector cap 202 is made of Amoco 40-17 polypropylene.

Figure 8:
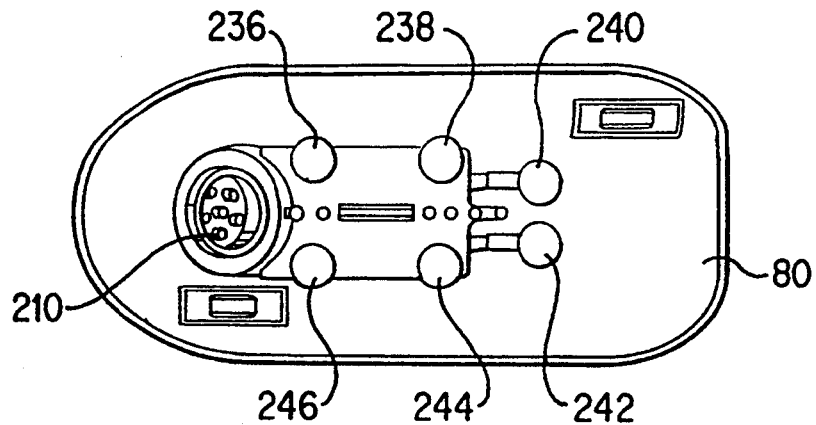
FIG. 8 is a plan view of the diagnostic port assembly.
Figure 9:
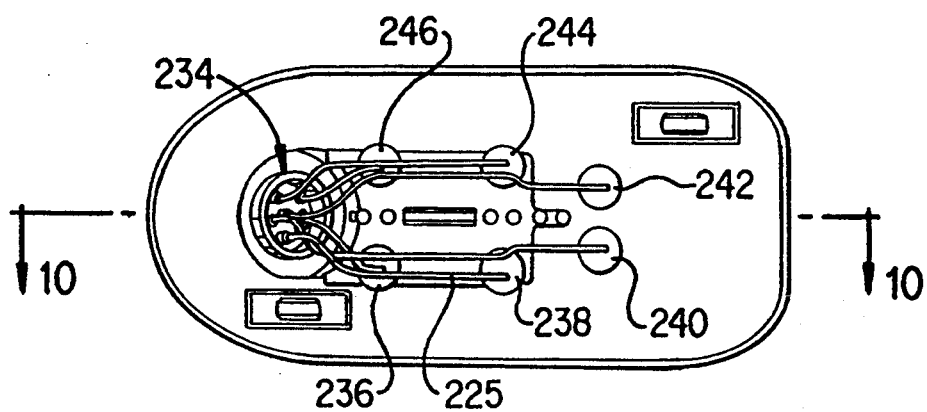
FIG. 9 is a bottom view of the pulse generator header.
Figures 10, 14:
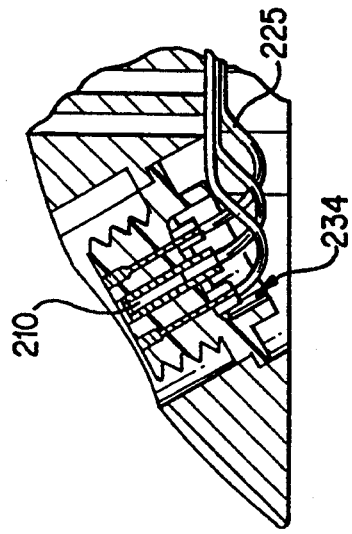
FIG. 10 is a sectional view taken along line 10—10 of FIG. 9.
FIG. 14 is a schematic view of a diagnostic port and connector block wiring diagram.

In FIG. 8, six different connector blocks are illustrated which, as shown in FIG. 9, are connected by wires routed to the rear 234 of the diagnostic connector port 84 and to the rear of the female contact receptacles 210. The connector blocks of FIG. 8 are the atrial tip connector block 236, the atrial ring connector block 238, the defibrillator negative connector block 240, the defibrillator positive connector block 242, the ventrical ring connector block 244 and the ventrical tip connector block 246. In FIG. 10, a cross sectional view of FIG. 9 illustrates the connection of wires 225 to the rear of the female contact pins 210.

Figure 11:
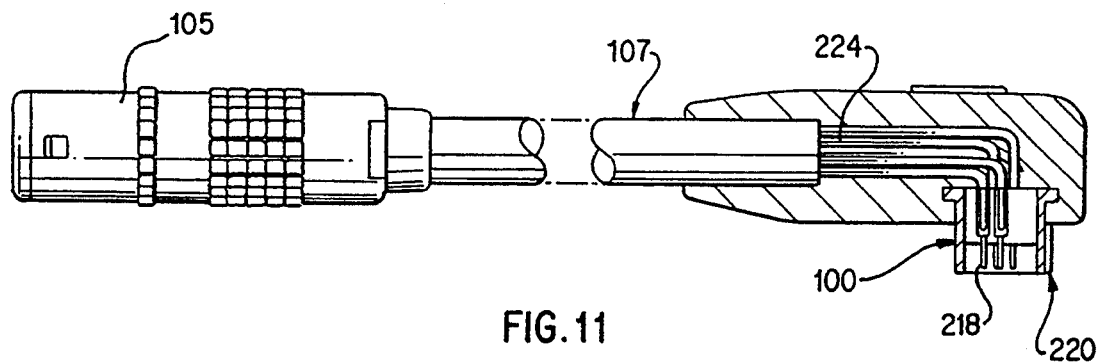
FIGS. 11–13 illustrate a sectional view, a bottom view and detailed view of a male connector plug for insertion into a diagnostic connector port having female contact receptacles.

In FIG. 11, a connector plug 100 is shown having a plurality of downwardly extending pins 218, each having a shape complementary to the female contact receptacle 210 of the diagnostic connector port 84 to form intimate contact with the receptacles 210 when the connector plug 100 is inserted into the port 84. The spacing of the receptacles 210 and pins 218 is such that the connector plug will fit into the diagnostic connector port in a single direction as aligned by key tab 220 so as to ensure a specific arrangement of alignment between pins for transmission of information from the pulse generator device to a receiving device in a specific arrangement.

The receptacles 210 are connected by wires 224 to a connector shell 105. The wires 224 form an output cable 107 formed of thermoplastic rubber (TPR) insulation.

Figure 12:
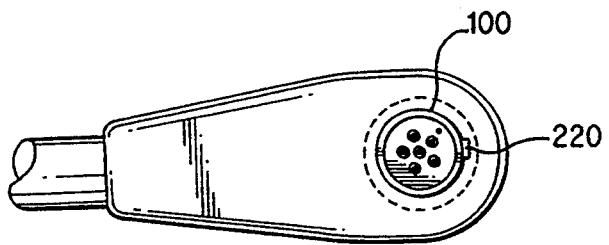
Figure 13:
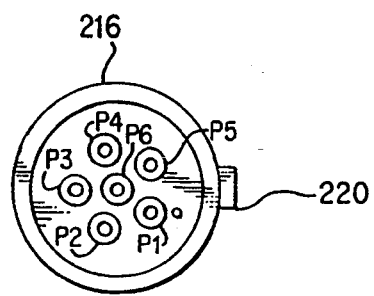

In FIGS. 12 and 13, the pins 218 are arranged in positions to engage only a corresponding receptacle of a diagnostic port for transfer of information to the output cable 107. A corresponding keyway 222 for the key tab 220 assures proper alignment of the connector plug 100.

FIG. 14 schematically illustrates the connection of pins 218 and contact receptacles 210 which are respectively connected to a connector block by wires 225. When the cable is plugged into the diagnostic port, aligned communication between the implantable pulse generator device 70 and output cable 107 having molded cable mounting block 214 is achieved.

In an alternate embodiment, as shown in FIGS. 15-20, the male contact pins and female contact receptacles are reversed from the orientation in the preferred embodiment and the male-type contact pins are located in the diagnostic connector port and are interconnected to a cable having female contact receptacles.

Figure 15:
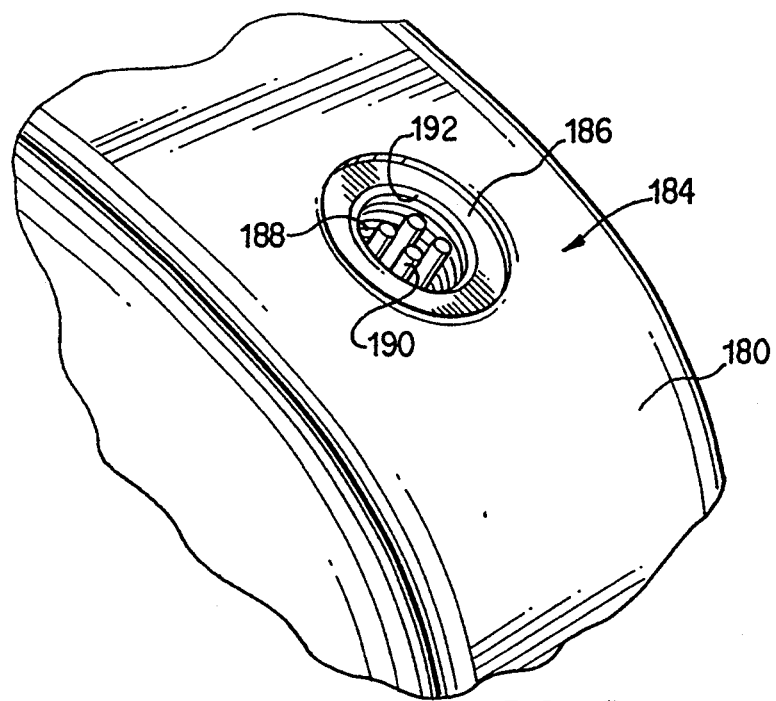
FIG. 15 is an enlarged view of a diagnostic connector port.

In FIG. 15, a detailed view of the diagnostic connector port 184 is shown. An uppermost surface 186 of the port is recessed slightly below the surface of the header 180 of a pulse generator device 170. Within a circular aperture 188 are located four contact pins 190 which are spaced radially inwardly from a threaded surrounding wall 192 of the aperture 188. This embodiment is formed by molding pins 190 directly in the header 180.

Figure 16:
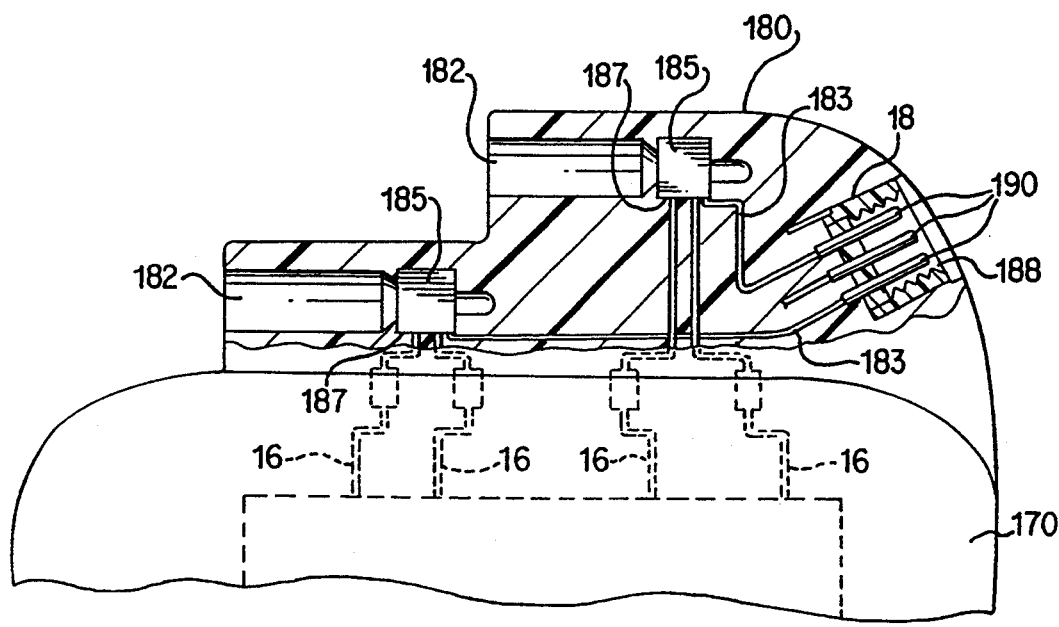
FIG. 16 is a partial sectional view of a pulse generator device having a diagnostic connector port.

In FIG. 16, a schematic connection of a molded-in diagnostic port connector is shown. Feed through wires 16 connect the electronics, batteries, capacitors, etc. of a hermetically sealed can of a pulse generator device 170 with the ports 182. Similarly connected to the ports 182 are pins 190 extending into opening 188 for connection with a connector plug. The interior wall 18 of the diagnostic connector port 184 is threaded to secure the diagnostic connector port cap within the molded header of the pulse generator device 170. The port itself is either welded, bonded or molded into the header.

A connector is welded or adhesively bonded into the header from the bottom side of the header. It is aligned to a keyway in the header via a 0.145" flat portion. Each of the six insulated platinum wires 183 is routed to the underside of connector blocks 185 and welded to a connector block surface 187. The header is installed in a traditional manner, i.e. it fits on the can of a pulse generator device 170 and allows the feed through wires 16 to be routed through the header 180 to the connector blocks 185. The feed through wires are welded on the connector blocks and sealed using medical adhesive. The device is now ready to be implanted.

During the implant procedure a cable is plugged into the diagnostic port and is keyed to facilitate insertion in the proper orientation. The keyway is in the header but could be a part of the port as well. After implant the port is sealed off using a cap and at least one gasket. A second gasket could be used as well but it is primarily a redundant gasket for additional safety. The facial gasket interfaces to the port on the flat surface of the port. The entire unit is then implanted in the patient (excluding cable).

In the embodiment in FIG. 16, a sealing plug is threaded into the opening 188 and around the pins 190 to seal the pins 190 against interaction with surrounding body fluids until it is time to connect a connector plug with the pins 190 to obtain signals indicative of the operation of the pulse generator device 170.

Figure 17:
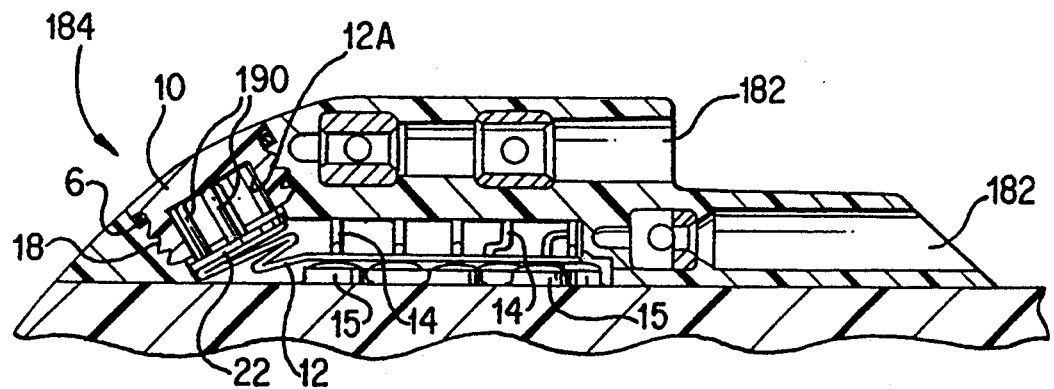
FIG. 17 is a sectional view of an alternate embodiment of a pulse generator device having a diagnostic connector port.
Figure 18:
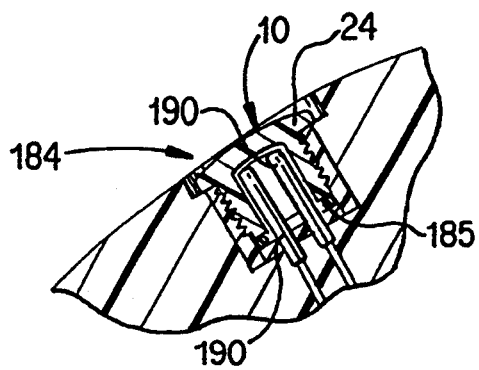
FIG. 18 is a sectional view of an alternate embodiment of a diagnostic connector port with a sealing plug.
Figure 19:
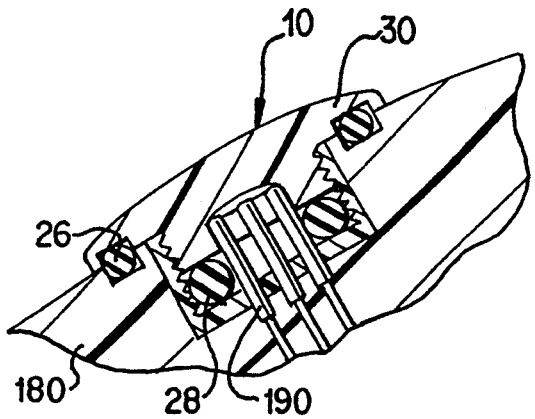
FIG. 19 is a sectional view of a diagnostic connector port with an alternate embodiment of a sealing plug.
Figure 20:
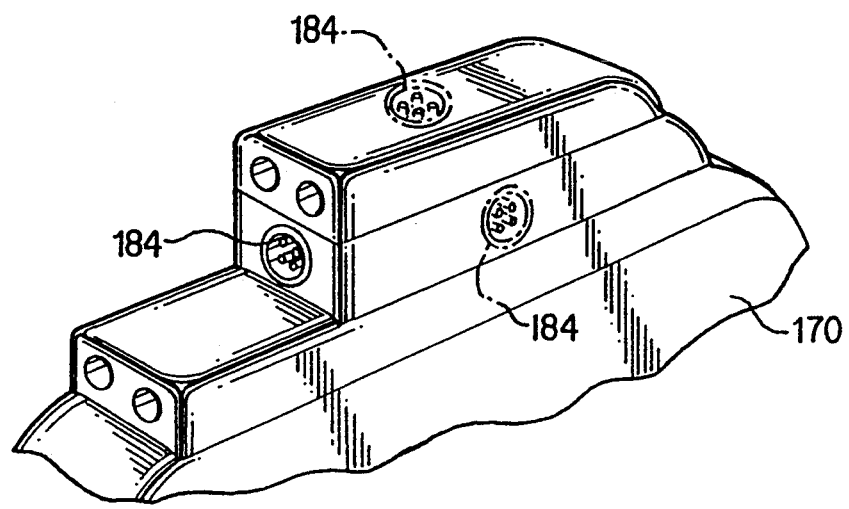
FIG. 20 illustrates alternate locations for a diagnostic connector port on a header of a pulse generator device.

In FIGS. 17 through 19, alternative sealing plugs 10 are shown.

In FIG. 17, the electrical connections to the pins 190 are made in the form of a flexible circuit 12 having a series of paths which are respectively connected to leads 14 which are connected to the leads inserted into ports 182. Similarly, feed throughs 15 extend into the hermetically sealed can of the pulse generator device.

A single O-ring 6 seals the sealing plug 10 when the sealing plug 10 is screwed into the interior threaded wall 18 of diagnostic connector port 184. The sealing plug 10 includes a central recess defined by an interior wall 12A to surround the pins 190 projecting from a plate 22 to which the flexible circuit 12 is electrically connected.

In FIG. 18, the sealing plug 10 is threaded into the diagnostic connector port 184. An O-ring 185 is located at the bottom of the sealing plug 10 to seal the sealing plug with respect to the diagnostic connector port. In this embodiment as well as in the other embodiments, the head 24 of the sealing plug 10 may be slotted to facilitate its removal for connection of a connector plug to the pins 190 of the diagnostic connector port.

In FIG. 19, two O-rings 26 and 28 are required to seal the sealing plug 10 against body fluids flowing into contact with the pins 190 during the time period when the diagnostic connector port 184 is not being used. In FIG. 19, the head 30 of the sealing plug projects above the surface of the header 180 of the pulse generator device.

The O-ring of FIGS. 17 through 19 may be made of silicon with the pins, as in the prior embodiments, made of stainless steel, NPS, platinum, gold, silver or other bio-compatible conductors. The remaining implantable diagnostic connector port 184 elements must be made of any bio-compatible material such as Pelletbane TM, epoxy or silicone, for example.

Figure 21:
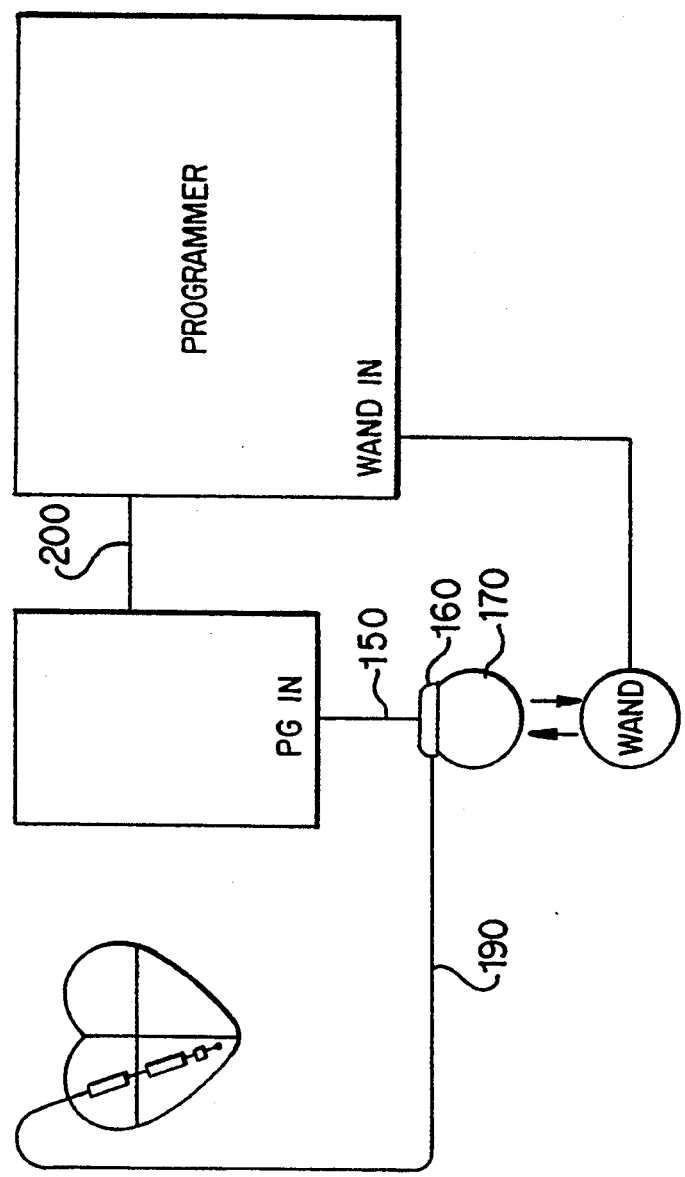
FIG. 21 is a schematic view of the interaction of a pulse generating device having a diagnostic connector port and the signals received by connection to a connector plug.

In FIG. 21, the connection of a connector plug is schematically shown by line 150 which is inserted into a diagnostic connector port of a header 160 of a pulse generator device 170. Line 190 is representative of a lead attached to an electrode connected to the heart for pulsing operations. The signals received by the connector plug are transferred by line 200 to a diagnostic equipment programmer for comparison with threshold requirements which may be varied according to the diagnostic information generated from the diagnostic connector port.

Having described the invention, many modifications thereto will become apparent to those skilled in the art to which it pertains without deviation from the spirit of the invention as defined by the scope of the appended claims.

I claim:

1. A pulse generator device comprising:
    a body including pulse means for generating charges transferred to a heart of a patient;
    a header on said body;
    a plurality of lead ports formed in said header for connection with leads extending to the heart to transfer charges to the heart from said body; and
    a diagnostic connector port formed in said header and being electrically connected to said lead ports;
    said diagnostic connector port including electrical contact means for electrically connecting said diagnostic connector port with connector plug means for transfer of information from said body directly to external diagnostic equipment during interengagement of said electrical contact means and said connector plug means.

2. A pulse generator as claimed in claim 1, wherein said electrical contact means includes a plurality of contact receptacles.

3. A pulse generator as claimed in claim 2, wherein said electrical contact means includes a number of receptacles corresponding to contact pins of contact connector plug means.

4. A pulse generator as claimed in claim 2, wherein said electrical contact means is keyed to fit a single way with said connector plug means.

5. A pulse generator as claimed in claim 1, wherein sealing means covers said diagnostic connector port and is removably mounted on said diagnostic connector port for protecting said diagnostic connector port from contact with surrounding body fluids.

6. A pulse generator as claimed in claim 5, wherein said sealing means includes a port cap.

7. A pulse generator as claimed in claim 6, wherein said sealing means includes a sealing plug located between said port cap and said diagnostic connector port for forcing fluid out of a diagnostic connector port.

8. A pulse generator as claimed in claim 6, wherein an uppermost surface of said port cap projects beyond a contour of said header.

9. A pulse generator as claimed in claim 6, wherein an uppermost surface of said port cap is recessed from a contour of said header.

10. A pulse generator as claimed in claim 6, wherein an uppermost surface of said port cap is continuous with a contour of said header.

11. A pulse generator as claimed in claim 6, wherein an O-ring is interposed between said port cap and said header preventing exposure of said electrical contact means to body fluids surrounding said header.

12. A pulse generator as claimed in claim 1, wherein said electrical contact means are electrically connected to said lead ports.

13. A pulse generator as claimed in claim 1, wherein said electrical contact means includes a plurality of contact pins.

14. A pulse generator device comprising:
    a body including pulse means for generating charges transferred to a heart of a patient;
    a header mounted on said body;
    a plurality of lead ports formed in said header for connection with leads extending to the heart to transfer charges to the heart from said body; and
    a diagnostic connector port, said pulse means and said plurality of lead ports being electrically connected to each other and being electrically connected to said diagnostic connector port;
    said diagnostic connector port including electrical contact means for electrically connecting said diagnostic connector port with connector plug means for transfer of information from said body directly to external diagnostic equipment during interengagement of said electrical contact means and said connector plug means.

15. A pulse generator as claimed in claim 14, wherein said electrical contact means includes a plurality of contact receptacles.

16. A pulse generator as claimed in claim 14, wherein sealing means covers said diagnostic connector port and is removably mounted on said diagnostic connector port for protecting said diagnostic connector port from contact with surrounding body fluids.

17. A pulse generator as claimed in claim 16, wherein said sealing means includes a port cap.

18. A pulse generator as claimed in claim 17, wherein said sealing means includes a sealing plug located between said port cap and said diagnostic connector port for forcing fluid out of the diagnostic connector port.

19. A pulse generator as claimed in claim 17, wherein an O-ring is interposed between said port cap and said header preventing exposure of said electrical contact means to body fluids surrounding said header.

20. A pulse generator as claimed in claim 15, wherein said electrical contact means includes a number of receptacles corresponding to contact pins of connector plug means.

21. A pulse generator as claimed in claim 14, wherein said electrical contact means is keyed to fit in a single way with said connector plug means.

22. A pulse generator as claimed in claim 14, wherein said electrical contact means are electrically connected to said lead ports.

* * * * *